(12) United States Patent
Seaward et al.

(10) Patent No.: US 7,173,240 B2
(45) Date of Patent: Feb. 6, 2007

(54) ELECTROSPRAY DEVICES FOR MASS SPECTROMETRY

(75) Inventors: Karen L. Seaward, Palo Alto, CA (US); Hongfeng Yin, Cupertino, CA (US); Kevin P. Killeen, Palo Alto, CA (US); Daniel Sobek, Portola Valley, CA (US); Daniel Roitman, Menlo Park, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 86 days.

(21) Appl. No.: 11/001,268

(22) Filed: Nov. 30, 2004

(65) Prior Publication Data

US 2006/0097153 A1    May 11, 2006

Related U.S. Application Data

(63) Continuation-in-part of application No. 10/982,189, filed on Nov. 5, 2004.

(51) Int. Cl.
   *H01J 49/10*    (2006.01)
(52) U.S. Cl. .................... 250/288; 250/423 R
(58) Field of Classification Search .............. 250/288, 250/423 R, 424
   See application file for complete search history.

(56) References Cited

U.S. PATENT DOCUMENTS 5,872,010 A    2/1999    Karger et al.

2003/0180965 A1*    9/2003    Yobas et al. .............. 436/180
2006/0049347 A1*    3/2006    Joyce et al. .............. 250/288
2006/0097145 A1*    5/2006    Joyce et al. .............. 250/284

FOREIGN PATENT DOCUMENTS

WO    WO 2004/079364    9/2004

OTHER PUBLICATIONS

Griss et al., Development of micromachined hollow tips for protein analysis based on nanoelectrospray ionization mass spectrometry, J. Micromech. Microeng. 12 (2002) 682-687.
Ramsey et al., Generating Electrospray from Microchip Devices Using Electroosmotic Pumping, Anal. Chem. 1997, 69, 1174-1178.
Svedberg et al., Sheathless Electrospray from polymer Microchips, Anal. Chem. 2003, 75, 3934-3940.
Yuan et al., Sequential Electrospray Analysis Using Sharp-Tip Channels Fabricated on a Plastic Chip, Anal. Chem. 2001, 73, 1080-1083.
Xue et al., Multichannel Microchip Electrospray Mass Spectrometry, Anal. Chem. 1997, 69, 426-430.

* cited by examiner

*Primary Examiner*—Kiet T. Nguyen

(57) ABSTRACT

An electrospray device for a mass spectrometry system is described. The electrospray device comprises a body portion and a tip portion extending from the body portion. The tip portion comprises a polymeric material. The electrospray device also comprises a hydrophobic coating substantially selectively covering the tip portion.

16 Claims, 2 Drawing Sheets

ELECTROSPRAY DEVICES FOR MASS SPECTROMETRY

CROSS REFERENCE TO RELATED APPLICATION

This application is a continuation-in-part of U.S. patent application Ser. No. 10/982,189, filed Nov. 5, 2004, the disclosure of which is incorporated herein by reference in its entirety.

TECHNICAL FIELD

The technical field of the invention relates to analytical instruments and, in particular, to mass spectrometry.

BACKGROUND

Various analytical instruments can be used for analyzing proteins and other biomolecules. More recently, mass spectrometry has gained prominence because of its ability to handle a wide variety of biomolecules with high sensitivity and rapid throughput. A variety of ion sources have been developed for use in mass spectrometry. Many of these ion sources comprise some type of mechanism that produces charged species through spraying. One particular type of technique that is often used is Electrospray Ionization ("ESI"). One benefit of ESI is its ability to produce charged species from a wide variety of biomolecules such as proteins. Another benefit of ESI is that it can be readily used in conjunction with a wide variety of chemical separation techniques, such as High Performance Liquid Chromatography ("HPLC"). For example, ESI is often used in conjunction with HPLC for identifying proteins.

Typically, ESI produces a spray of ions in a gaseous phase from a sample stream that is initially in a liquid phase. For a conventional ESI mass spectrometry system, a sample stream is pumped through an electrospray device, while a relatively high electric field is applied between an end of the electrospray device and an electrode that is positioned adjacent to the end of the electrospray device. As the sample stream exits through the end of the electrospray device, surface charges are produced in the sample stream, thus pulling the sample stream towards the electrode. As the sample stream enters the high electric field, a combined electro-hydrodynamic force on the sample stream is balanced by its surface tension, thus producing a "Taylor cone." Typically, the Taylor cone has a base positioned near the end of the electrospray device and extends up to a certain distance away from the end of the electrospray device, beyond which a spray of droplets is produced. As these droplets move towards the electrode, coulombic repulsive forces and desolvation lead to the formation of a spray of ions in a gaseous phase.

Characteristics of a Taylor cone typically depend on an affinity between a sample stream and a surface at an end of an electrospray device. Depending on this affinity, a greater or lesser area of the surface can be wetted by the sample stream, which, in turn, can affect a volume of the Taylor cone. A Taylor cone with a larger volume can present a number of disadvantages. In particular, the larger volume of the Taylor cone can translate into a larger volume of a sample stream that is required for mass spectrometric analysis, which can be problematic when analyzing proteins and other biomolecules that are present in small quantities. Also, the larger volume of the Taylor cone can create a "dead volume" within which internal fluid circulation can occur. Within this "dead volume," distinct bands of sample streams can merge, thus compromising band resolution. In addition, the larger volume of the Taylor cone can reduce ionization efficiency. Accordingly, for these and other reasons, it is desirable to reproducibly produce Taylor cones with low volumes, such that results of mass spectrometric analysis have a desired level of accuracy, reproducibility, and sensitivity.

Recently, attempts have been made to implement polymeric devices as electrospray devices for use in mass spectrometry. Such polymeric devices are desirable, since they can be precisely shaped using a wide variety of techniques. One of the challenges to successfully implementing such polymeric devices relates to an affinity between a sample stream and polymeric materials that are typically used to form these polymeric devices. In particular, this affinity can promote formation of Taylor cones with larger volumes, which can be disadvantageous for the reasons described above.

SUMMARY

The invention provides a mass spectrometry system. The mass spectrometry system comprises an ion source comprising an electrospray device configured to pass a sample stream. The electrospray device comprises a body portion and a tip portion extending from the body portion. The tip portion comprises a polymeric material. The electrospray device also comprises a coating at least partly covering the tip portion, while the body portion is substantially uncovered by the coating. The coating provides a hydrophobic surface. The ion source also comprises an electrode positioned with respect to the electrospray device, wherein, when a voltage between the electrospray device and the electrode is applied, ions are produced from the sample stream and are directed towards the electrode. The mass spectrometry system also comprises a detector positioned with respect to the ion source to detect the ions.

The invention also provides an ion source for a mass spectrometry system. The ion source comprises an electrospray device comprising a polymeric tip portion, and the polymeric tip portion is elongated and defines a conduit configured to pass a sample stream. The electrospray device also comprises a hydrophobic coating at least partly covering the polymeric tip portion. The ion source also comprises an electrode positioned adjacent to the electrospray device. The ion source further comprises a power source in electrical connection with the electrospray device and the electrode. The power source is configured to apply a voltage between the electrospray device and the electrode to produce ions from the sample stream.

The invention further provides an electrospray device for a mass spectrometry system. The electrospray device comprises a body portion and a tip portion extending from the body portion. The tip portion comprises a polymeric material. The electrospray device also comprises a hydrophobic coating substantially selectively covering the tip portion.

Advantageously, embodiments of the invention allow Taylor cones to be produced with reproducible characteristics, such that results of mass spectrometric analysis have a desired level of accuracy, reproducibility, and sensitivity. For some embodiments of the invention, reproducibility of Taylor cones can be achieved by using a coating that is highly hydrophobic and that is selectively deposited on an electrospray device.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWINGS

For a better understanding of the nature and objects of some embodiments of the invention, reference should be made to the following detailed description taken in conjunction with the accompanying drawings.

DETAILED DESCRIPTION

Definitions

Figure 1:
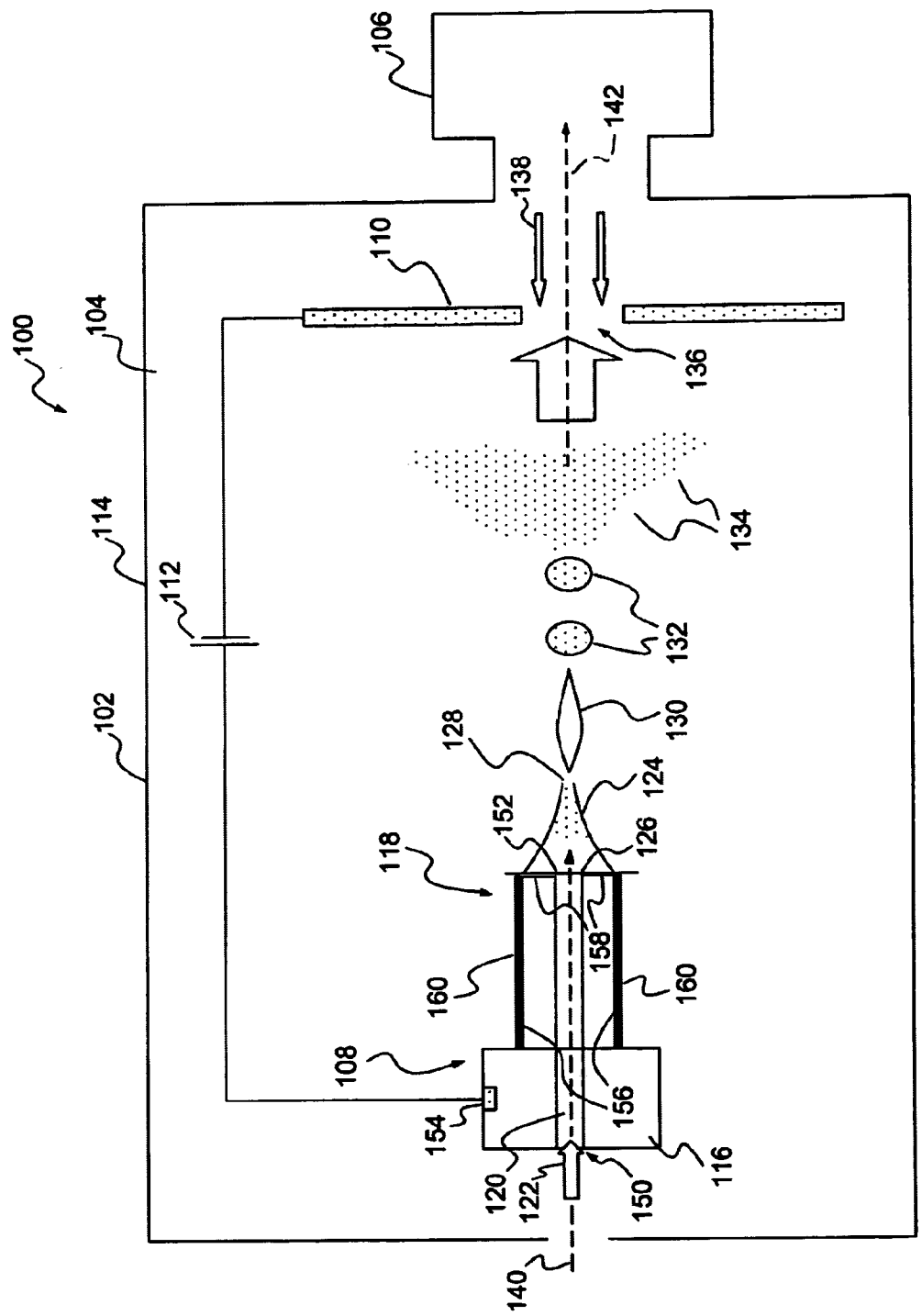
FIG. 1 illustrates a mass spectrometry system implemented in accordance with an embodiment of the invention.

The following definitions apply to some of the elements described with respect to some embodiments of the invention. These definitions may likewise be expanded upon herein.

As used herein, the singular terms "a," "an," and "the" comprise plural referents unless the context clearly dictates otherwise. Thus, for example, reference to a material can comprise multiple materials unless the context clearly dictates otherwise.

As used herein, the term "set" refers to a collection of one or more elements. Thus, for example, a set of features can comprise a single feature or multiple features. Elements of a set can also be referred to as members of the set. Elements of a set can be the same or different. In some instances, elements of a set can share one or more common characteristics.

As used herein, the terms "hydrophilic" and "hydrophilicity" refer to an affinity for water, while the terms "hydrophobic" and "hydrophobicity" refer to a lack of affinity for water. Hydrophobic materials typically correspond to those materials to which water has little or no tendency to adhere. As such, water on a surface of a hydrophobic material tends to bead up. Hydrophobic materials can sometimes be referred to as non-wetting materials. One measure of hydrophobicity of a material is a contact angle between a surface of the material and a line tangent to a drop of water at a point of contact with the surface. According to such measure, the material is typically considered to be hydrophobic if the contact angle is greater than 90°. Another measure of hydrophobicity of a material is a surface energy of the material expressed in milli-Newtons/meter ("mN/m"). According to such measure, the material is typically considered to be hydrophobic if its surface energy is less than 20 mN/m.

As used herein, the terms "electrically conductive" and "electrical conductivity" refer to an ability to transport an electric current, while the terms "electrically nonconductive" and "electrical nonconductivity" refer to a lack of ability to transport an electric current. Electrically conductive materials typically correspond to those materials that exhibit little or no opposition to flow of an electric current, while electrically nonconductive materials typically correspond to those materials within which an electric current has little or no tendency to flow. One measure of electrical conductivity (or electrical nonconductivity) of a material is its resistivity expressed in ohm.centimeter ("Ω·cm"). Typically, the material is considered to be electrically conductive if its resistivity is less than 0.001 Ω·cm, while the material is considered to be electrically nonconductive if its resistivity is greater than 0.001 Ω·cm. The resistivity of a material can sometimes vary with temperature. Thus, unless otherwise specified, the resistivity of a material is defined at room temperature.

As used herein, the terms "inert" and "inertness" refer to a lack of interaction. Inert materials typically correspond to those materials that exhibit little or no tendency to interact with a sample stream under typical operating conditions, such as typical operating conditions of the electrospray devices described herein. Typically, inert materials also exhibit little or no tendency to interact with a spray of droplets or a spray of ions produced from a sample stream in accordance with an ionization process. While a material is sometimes referred to herein as being inert, it is contemplated that the material can exhibit some detectable tendency to interact with a sample stream under certain conditions. One measure of inertness of a material is its chemical reactivity. Typically, the material is considered to be inert if it exhibits little or no chemical reactivity with respect to a sample stream.

As used herein, the terms "robust" and "robustness" refer to a mechanical hardness or strength. Robust materials typically correspond to those materials that exhibit little or no tendency to fragment under typical operating conditions, such as typical operating conditions of the electrospray devices described herein. One measure of robustness of a material is its Vicker microhardness expressed in kilogram/millimeter ("kg/mm"). Typically, the material is considered to be robust if its Vicker microhardness is greater than 1,000 kg/mm.

As used herein, the term "ionization efficiency" refers to a ratio of the number of ions formed in an ionization process and the number of analyte molecules used in the ionization process.

As used herein, the terms "integrated," "integral," and "integrally" refer to a non-discrete portion of an object. Thus, for example, an electrospray device comprising a body portion and a tip portion that is formed integrally with the body portion can refer to an implementation of the electrospray device in which the body portion and the tip portion are formed as a monolithic unit. An integrated portion of an object can differ from one that is attached to the object, since the integrated portion of the object typically does not form an interface with a remaining portion of the object.

As used herein, the term "microdevice" refers to a device that comprises a set of features with at least one dimension in the micron or sub-micron range. A microdevice can be used for a wide variety of applications, such as mass spectrometry, electrophoresis, chromatography, chemical screening and diagnostics, biochemical screening and diagnostics, chemical synthesis, biochemical synthesis, and so forth. For example, a microdevice can be used as an electrospray device and can comprise a set of features such as an inlet port, an outlet port, a conduit, an electrode, and so forth. Features of a microdevice are typically implemented in accordance with a particular application of the microdevice. For example, when used as an electrospray device, a microdevice can comprise a conduit that has a cross-sectional diameter from about 1 micrometer ("μm") to about 200 μm, such as from about 5 μm to about 75 μm, and a length from about 0.1 cm to about 100 cm. For certain applications, a microdevice can comprise a set of sample preparation regions or reaction zones that can each comprise a volume from about 1 nanoliter ("nl") to about 1,000 nl, such as from about 10 nl to about 200 nl. Microdevices can be formed using a wide variety of techniques, such as laser ablation, photochemical etching, plasma etching, chemical etching, electrochemical etching, ion milling, electron beam etching, photoresist masking, dry etching, wet etching, molding, embossing, and so forth. Laser ablation can be a particularly desirable technique, since it allows for dimensionally precise shaping of a microdevice. Laser ablation typically involves use of a high-energy laser, such as a solid state laser or an excimer laser of $F_2$, ArF, KrCl, KrF, or XeCl. In some instances, laser ablation involves use of pulse energies that are greater than about 100 millijoules per square centimeter and pulse durations that are shorter than about 1 microsecond. Photochemical etching can be another particularly desirable technique to form a microdevice. In photochemical etching, dimensionally precise shaping of an object can be achieved by immersing the object in a chemical etchant and directing optical energy, such as from a laser, to selected portions of the object so as to remove those portions.

Attention first turns to FIG. 1, which illustrates a mass spectrometry system 100 implemented in accordance with an embodiment of the invention. The mass spectrometry system 100 comprises an ion source 102, which operates to produce ions. In the illustrated embodiment, the ion source 102 operates to produce ions using ESI. However, it is contemplated that the ion source 102 can be implemented to produce ions using any other ionization process. As illustrated in FIG. 1, the mass spectrometry system 100 also comprises a detector 106, which is positioned with respect to the ion source 102 to receive ions. The detector 106 operates to detect ions as a function of mass and charge.

In the illustrated embodiment, the ion source 102 comprises an electrospray device 108 and an electrode 110, which is positioned adjacent to the electrospray device 108. The ion source 102 also comprises a power source 112, which is electrically connected to the electrospray device 108 and to the electrode 110. The power source 112 operates to apply a voltage to the electrospray device 108 and to the electrode 110, thus producing an electric field between the electrospray device 108 and the electrode 110. As illustrated in FIG. 1, the ion source 102 also comprises a housing 114, which defines an internal chamber 104 within which the electrospray device 108, the electrode 110, and the power source 112 are positioned.

As illustrated in FIG. 1, the electrospray device 108 is implemented as a microdevice. In particular, the electrospray device 108 comprises a body portion 116 and a tip portion 118, which is elongated and serves as an electrospray emitter. The tip portion 118 extends from the body portion 116 and comprises a relatively small cross-sectional area, which serves to promote formation of a Taylor cone with a low volume. The tip portion 118 can comprise any of a wide variety of cross-sectional shapes, such as circular, triangular, square-shaped, rectangular, and so forth. In the illustrated embodiment, the tip portion 118 is formed integrally with the body portion 116. Such implementation can be desirable to avoid formation of an interface between the tip portion 118 and the body portion 116. As can be appreciated, this interface can create an undesirable mixing volume and can be a source of contamination when using adhesives to attach the tip portion 118 to the body portion 116. However, it is contemplated that the tip portion 118 can be attached to the body portion 116 for other embodiments of the invention.

In the illustrated embodiment, the electrospray device 108 comprises a set of features, namely an inlet port 150, an outlet port 152, a conduit 120, and an electrode 154. While not illustrated in FIG. 1, it is contemplated that the electrospray device 108 can comprise one or more additional features, such as a sample preparation region or a reaction zone. As illustrated in FIG. 1, the body portion 116 comprises the electrode 154, which serves as a counter-electrode with respect to the electrode 110. The body portion 116 defines the inlet port 150 through which a sample stream 122 enters the electrospray device 108. The sample stream 122 comprises analytes to be analyzed by the mass spectrometry system 100. For example, the sample stream 122 can comprise biomolecules that are dispersed in a suitable solvent, such as water. In conjunction with the tip portion 118, the body portion 116 also defines the conduit 120 through which the sample stream 122 passes. As illustrated in FIG. 1, the tip portion 118 defines the outlet port 152 through which the sample stream 122 exists the electrospray device 108. The tip portion 118 comprises a set of side surfaces 156 and a terminus surface 158, which is positioned adjacent to the outlet port 152. While the set of side surfaces 156 and the terminus surface 158 are illustrated as being generally planar, it is contemplated that one or more of these surfaces can be curved.

In general, the electrospray device 108 can be formed using any of a wide variety of materials, such as polymeric materials, ceramics, glasses, metals, and composites or laminates thereof. In the illustrated embodiment, at least the tip portion 118 of the electrospray device 108 is formed using a polymeric material, which allows the tip portion 118 to be precisely shaped using any of a wide variety of techniques. It is contemplated that the body portion 116 can be formed using the same polymeric material or a different polymeric material. Polymeric materials can comprise homopolymers, copolymers, naturally occurring polymers, synthetic polymers, crosslinked polymers, uncrosslinked polymers, and mixtures thereof. Specific examples of polymeric materials comprise polyimides, polyketones such as polyetheretherketones, polycarbonates, polyesters, polyamides, polyethers, polyurethanes, polyfluorocarbons, polystyrenes, poly(acrylonitrile-butadiene-styrene), acrylate and acrylic acid polymers such as polymethyl methacrylates, substituted and unsubstituted polyolefins, and mixtures or copolymers thereof. Polyimides and polyketones can be particularly desirable due to their resistance to biofouling. Polyimides are commercially available under the tradename Kapton® (DuPont, Wilmington, Del.) and Upilex® (Ube Industries, Ltd., Japan).

In the illustrated embodiment, the positioning of the electrospray device 108 in the vicinity of the electrode 110 at a negative bias produces an electric field gradient at the tip portion 118 of the electrospray device 108. As the sample stream 122 exits through the outlet port 152, a jump in displacement flux density produces surface charges in the sample stream 122, which pulls the sample stream 122 towards the electrode 110. In conjunction, a combined electro-hydrodynamic force on the sample stream 122 is balanced by its surface tension, thus producing a Taylor cone 124. As illustrated in FIG. 1, the Taylor cone 124 comprises a base 126 positioned near the terminus surface 158 of the tip portion 118. The Taylor cone 124 also comprises a tip 128, which extends into a filament 130. As the filament 130 extends further towards the electrode 110, combined effects of surface tension, coulombic repulsive forces, and small perturbations cause the filament 130 to break up and to form a spray of droplets 132. As these droplets 132 move towards the electrode 110, coulombic repulsive forces and desolvation lead to the formation of a spray of ions 134.

As illustrated in FIG. 1, the electrode 110 defines an aperture 136 near its center. The ions 134 pass through the electrode 110 via the aperture 136 and eventually reach the detector 106. In the illustrated embodiment, a drying gas 138, such as a nitrogen gas, flows in a direction counter to the ions 134 to improve ionization efficiency and to restrain introduction of undesirable materials into the aperture 136. In the illustrated embodiment, the electrode 110 is positioned in a longitudinal relationship with respect to the electrospray device 108. In other words, an angle defined by a central axis 140 of the conduit 120 and a central axis 142 of the aperture 136 is substantially at 0°. However, it is contemplated that this angle can be adjusted to differ from 0°, such as from about 75° to about 105°. For example, it is contemplated that the electrode 110 can be positioned in an orthogonal relationship with respect to the electrospray device 108, such that this angle is substantially at 90°.

During operation of the mass spectrometry system 100, characteristics of the Taylor cone 124 can affect characteristics of the ions 134 that are produced, which, in turn, can affect results of mass spectrometric analysis. Accordingly, it is desirable to produce Taylor cones with reproducible characteristics, such that results of mass spectrometric analysis have a desired level of accuracy, reproducibility, and sensitivity. In the illustrated embodiment, Taylor cones can be produced with reproducible characteristics by controlling hydrophobicity of the tip portion 118 of the electrospray device 108. In particular, if the set of side surfaces 156 are made sufficiently hydrophobic, the base 126 of the Taylor cone 124 can be restrained from spreading along the set of side surfaces 156. In such manner, the Taylor cone 124 can be reproducibly produced with a low volume.

As illustrated in FIG. 1, the electrospray device 108 comprises a hydrophobic coating 160 that at least partly covers the tip portion 118, which serves as a substrate. In general, the hydrophobic coating 160 can be formed using any of a wide variety of techniques. It has been discovered that plasma deposition can be a particularly desirable technique to form the hydrophobic coating 160. Typically, plasma deposition involves heating or electrical breakdown of a set of reactant gases to form a plasma, which is deposited on a substrate to form a coating, such as in the form of a polymeric film. Examples of reactant gases that can be used comprise fluorocarbons, such as $C_3F_8$, hydrocarbons, such as $CH_4$, gases that fragment to form fluorocarbons or hydrocarbons, such as $(CF_3)_2CO$ and hexamethyl disiloxane ("HMDSO"), fluorine-containing gases, such as $SF_6$, and mixtures thereof. By appropriate selection of a set of reactant gases and other processing conditions, the hydrophobic coating 160 can exhibit a number of desirable characteristics, such as in terms of hydrophobicity, inertness, robustness, electrical nonconductivity, and so forth.

In particular, the hydrophobic coating 160 can be highly hydrophobic, such that Taylor cones can be reproducibly produced with low volumes. In particular, the hydrophobic coating 160 can provide a hydrophobic surface that exhibits a contact angle with respect to water that is greater than 90°, such as greater than about 100°, greater than about 105°, or greater than about 110°. Alternatively, or in conjunction, the hydrophobic surface can exhibit a surface energy that is less than 20 mN/m, such as less than about 15 mN/m, less than about 10 mN/m, or less than about 5 mN/m. By appropriate selection of processing conditions, a degree of hydrophobicity can be readily tuned to a desired level. Also, the hydrophobic coating 160 can be highly inert and, thus, can exhibit little or no tendency to interact with the analytes comprising the sample stream 122. In addition, the hydrophobic coating 160 can be highly robust. Accordingly, the hydrophobic coating 160 can exhibit little or no tendency to fragment under typical operating conditions of the electrospray device 108, thus increasing operational lifetime of the electrospray device 108. Also, the hydrophobic coating 160 can be electrically nonconductive and can comprise a resistivity that is greater than 0.001 $\Omega\cdot cm$, such as greater than about 0.01 $\Omega\cdot cm$, greater than about 0.1 $\Omega\cdot cm$, or greater than about 1 $\Omega\cdot cm$. For certain implementations, a higher resistivity of the hydrophobic coating 160 can serve to avoid electrical discharges that can adversely affect an ionization process. However, it is also contemplated that the hydrophobic coating 160 can be electrically conductive. By appropriate selection of processing conditions, a resistivity of the hydrophobic coating 160 can be readily tuned to a desired level.

Another benefit of plasma deposition is that this technique allows precise control over which surface of a substrate should be coated and which surface of the substrate should remain uncoated. Such control can be achieved by, for example, using masks or proper positioning of the substrate within a plasma tool. As illustrated in FIG. 1, the hydrophobic coating 160 substantially selectively covers the tip portion 118, while the body portion 116 is substantially uncovered. In particular, the hydrophobic coating 160 is deposited so as to substantially selectively cover the set of side surfaces 156. In such fashion, hydrophobicity of the set of side surfaces 156 can be controlled without adversely affecting operation of a remaining portion of the electrospray device 108, such as the electrode 154. While FIG. 1 illustrates the hydrophobic coating 160 as covering the set of side surfaces 156, it is contemplated that the hydrophobic coating 160 can also at least partly cover the terminus surface 158. Such implementation can serve to restrain the base 126 of the Taylor cone 124 from spreading along the terminus surface 158. In such manner, the Taylor cone 124 can be reproducibly produced with a further reduced volume.

While plasma deposition can be a particularly desirable technique, it is contemplated that other techniques can be used to form the hydrophobic coating 160. For example, a hydrophobic material can be sprayed onto the tip portion 118, such that the hydrophobic material mechanically adheres to the tip portion 118. As another example, a hydrophobic material can be dispersed in a suitable solvent to form a "paint," and this paint can be applied to the tip portion 118. In some instances, the solvent can be relatively inert. However, it is also contemplated that the solvent can facilitate chemical bonding between the hydrophobic material and the tip portion 118. Heat can be applied to evaporate the solvent or to promote chemical bonding. As further examples, the hydrophobic coating 160 can be formed as a wiped-on coating or a dipped-on coating.

EXAMPLES

The following examples describe specific aspects of some embodiments of the invention to illustrate and provide a description of those embodiments for one of ordinary skill in the art. The examples should not be construed as limiting the invention, as the examples merely provide specific methodology useful in understanding and practicing some embodiments of the invention.

Example 1

Figure 2:
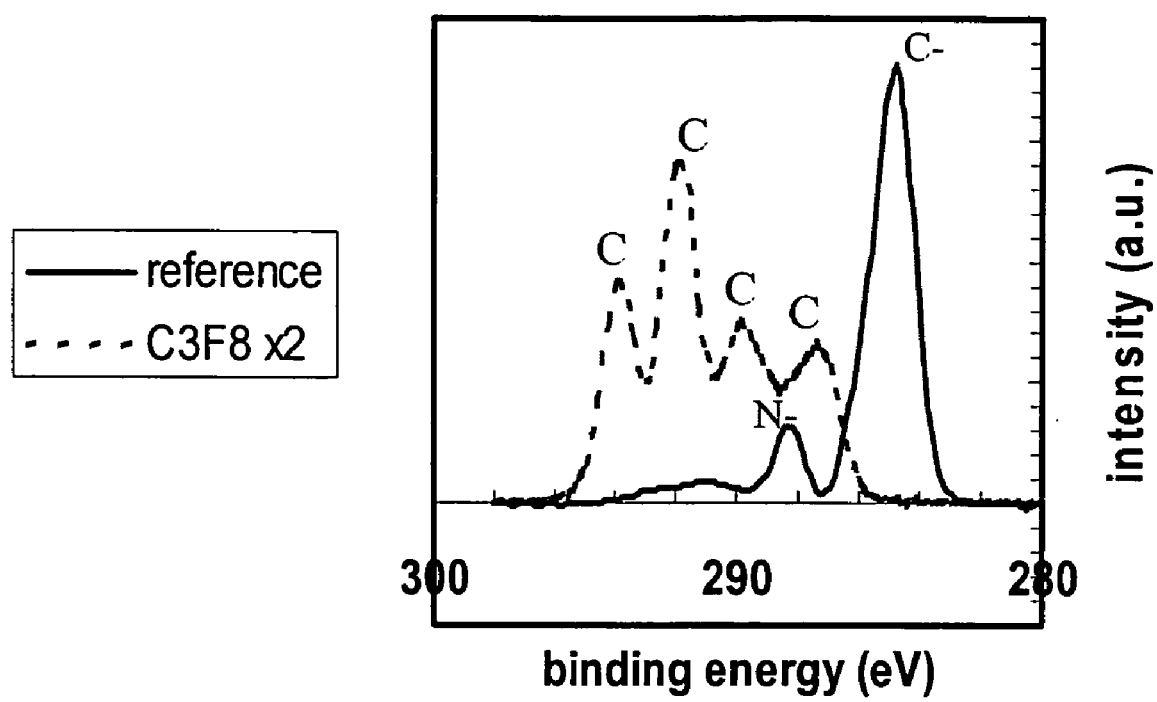
FIG. 2 illustrates Xray Photoelectron Spectroscopy ("XPS") data of polyimide surfaces with no treatment and with fluorocarbon plasma treatment, according to an embodiment of the invention.

A polyimide surface was treated with a fluorocarbon plasma ($C_3F_8$) using a parallel plate plasma tool. Surface chemistries of the treated polyimide surface and an untreated polyimide surface were measured using XPS and were found to differ after fluorocarbon plasma treatment, as illustrated in FIG. 2. The XPS data indicate that different chemical binding states were present in the treated and untreated polyimide surfaces. The treated polyimide surface comprised a variety of fluorocarbon species (e.g., C of CCF at 287.2 eV, C of CF at 289.7 eV, C of $CF_2$ at 291.8 eV, and C of $CF_3$ at 293.7 eV), while the untreated polyimide surface comprised aromatic rings (e.g., C=C at 285 eV) and carbonyls (e.g., C=O at 288.6 eV) of polyimide. A substantial $CF_2$ peak observed for the treated polyimide surface provides an indication that a resulting coating had a character similar to that of Teflon. A contact angle measurement for the treated polyimide surface showed a contact angle of 110° after fluorocarbon plasma treatment.

Example 2

Hydrophobic coatings were deposited on polymeric tip portions of electrospray devices by masking the electrospray devices except for a few millimeters from ends of the tip portions. The masked electrospray devices were placed in a plasma tool, and a $C_3F_8$ plasma was ignited for a period of minutes at moderate pressure and power. As a specific example, a hydrophobic coating was deposited using 15 sccm $C_3F_8$, 500 milli-Torr, and 100 Watts. Very stable electrospray behavior was observed after deposition of the hydrophobic coating. In addition, an onset potential of stable spray was reduced.

It should be recognized that the embodiments of the invention described above are provided by way of example, and various other embodiments are encompassed by the invention. For example, it is contemplated that the electrospray devices described herein can be advantageously used in conjunction with a control mechanism to regulate a spray of ions. One example of such a control mechanism is a feedback controller as described in the co-pending and co-owned patent application of Sobek, U.S. patent application Ser. No. 10/896,981, filed Jul. 23, 2004, entitled "Ion Source Frequency Feedback Device and Method," the disclosure of which is incorporated herein by reference in its entirety.

A practitioner of ordinary skill in the art requires no additional explanation in developing the electrospray devices described herein but may nevertheless find some helpful guidance by examining the following references: Taylor G. I., "Disintegration of Water Drops in an Electric Field," *Proceedings of the Royal Society of London*, A280, pp. 383–397, 1964; Bruins A. P., "Mechanistic Aspects of Electrospray Ionization," *Journal of Chromatography A,* 794, pp. 345–347, 1998; Juraschek et al., "Pulsation Phenomena During Electrospray Ionization," *International Journal of Mass Spectrometry,* 177, pp. 1–15, 1998; Cech et al., "Practical Implications of Some Recent Studies in Electrospray Ionization Fundamentals," *Mass Spectrometry Reviews,* 20, pp. 362–387, 2001; and Lee et al., "Taylor Cone Stability and ESI Performance for LC-MS at Low Flow Rates," *Proceedings of the American Society of Mass Spectrometry,* 2002; the disclosures of which are incorporated herein by reference in their entireties.

A practitioner of ordinary skill in the art may also find some helpful guidance regarding plasma deposition by examining the following references: Inagaki N., "Plasma Surface Modification and Plasma Polymerization," Chapter 2—Section 2.4, Chapter 4—Section 4.7, Chapter 5, Chapter 6—Section 6.6, Lancaster: Technomic, 1996; and D'Agostino R., Favia P., and Fracassi F. eds., "Plasma Processing of Polymers," pp. 28, 129–146, and 221–230, Boston: Kluwer Academic, 1997; the disclosures of which are incorporated herein by reference in their entireties.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, process operation or operations, to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

We claim:

1. An electrospray device for a mass spectrometry system, comprising:
- (a) a body portion;
- (b) a tip portion extending from the body portion, the tip portion comprising a polymeric material selected from polyimides, polyketones, polycarbonates, polyesters, polyamides, polyethers, polyurethanes, polyfluorocarbons, polystyrenes, poly(acrylonitrile-butadiene-styrene), acrylate polymers, acrylic acid polymers, polyolefins, and copolymers thereof; and
- (c) a hydrophobic coating substantially selectively covering the tip portion.

2. The electrospray device of claim 1, wherein the tip portion is formed integrally with the body portion.

3. The electrospray device of claim 1, wherein the polymeric material is selected from polyimides and polyketones.

4. The electrospray device of claim 1, wherein the hydrophobic coating provides a hydrophobic surface, and the hydrophobic surface exhibits a contact angle with respect to water that is greater than 90°.

5. The electrospray device of claim 4, wherein the contact angle is greater than 105°.

6. The electrospray device of claim 1, wherein the hydrophobic coating at least partly covers the tip portion, while the body portion is substantially uncovered.

7. The electrospray device of claim 1, wherein the hydrophobic coating is formed by plasma deposition of a reactant gas selected from fluorocarbons, hydrocarbons, gases that fragment to form hydrocarbons, gases that fragment to form fluorocarbons, fluorine-containing gases, and mixtures thereof.

8. An ion source for a mass spectrometry system, comprising:
- (a) an electrospray device comprising:
  - (i) a polymeric tip portion, the polymeric tip portion being elongated and defining a conduit configured to pass a sample stream; and
  - (ii) a hydrophobic coating at least partly covering the polymeric tip portion, the hydrophobic coating providing a hydrophobic surface that comprises a surface energy less than 20 mN/m;
- (b) an electrode positioned adjacent to the electrospray device; and (c) a power source in electrical connection with the electrospray device and the electrode, the power source being configured to apply a voltage between the electrospray device and the electrode to produce ions from the sample stream.

9. The ion source of claim 8, wherein the electrospray device further comprises a body portion, and the polymeric tip portion extends from the body portion.

10. The ion source of claim 9, wherein the hydrophobic coating at least partly covers the polymeric tip portion, while the body portion is substantially uncovered.

11. The ion source of claim 8, wherein the polymeric tip portion comprises a side surface, and the hydrophobic coating at least partly covers the side surface.

12. The ion source of claim 8, wherein the polymeric tip portion comprises a terminus surface, and the hydrophobic coating at least partly covers the terminus surface.

13. The ion source of claim 8, wherein the surface energy is less than 15 mN/m.

14. The ion source of claim 8, wherein the hydrophobic coating is formed by plasma deposition of a reactant gas selected from fluorocarbons, hydrocarbons, gases that fragment to form hydrocarbons, gases that fragment to form fluorocarbons, fluorine-containing gases, and mixtures thereof.

15. A mass spectrometry system, comprising:
(a) an ion source comprising:
  (i) an electrospray device configured to pass a sample stream, the electrospray device comprising:
    (1) a body portion;
    (2) a tip portion extending from the body portion, the tip portion comprising a polymeric material; and
    (3) a coating at least partly covering the tip portion, while the body portion is substantially uncovered by the coating, the coating providing a hydrophobic surface and being formed by plasma deposition of a reactant gas selected from fluorocarbons, hydrocarbons, gases that fragment to form hydrocarbons, gases that fragment to form fluorocarbons, fluorine-containing gases, and mixtures thereof; and
  (ii) an electrode positioned with respect to the electrospray device, wherein, when a voltage between the electrospray device and the electrode is applied, ions are produced from the sample stream and are directed towards the electrode; and
(b) a detector positioned with respect to the ion source to detect the ions.

16. The mass spectrometry system of claim 15, wherein the coating comprises a surface energy that is less than 20 mN/m.

* * * * *